(12) United States Patent
Herr

(10) Patent No.: US 9,272,100 B2
(45) Date of Patent: Mar. 1, 2016

(54) EXTENDED HUB FOR A SAFETY PEN NEEDLE

(71) Applicant: Becton, Dickinson and Company, Franklin Lakes, NJ (US)

(72) Inventor: Joshua Herr, Fair Lawn, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 105 days.

(21) Appl. No.: 13/972,411

(22) Filed: Aug. 21, 2013

(65) Prior Publication Data

US 2015/0057637 A1    Feb. 26, 2015

(51) Int. Cl.
*A61M 5/46* (2006.01)
*A61M 5/32* (2006.01)
*A61M 5/34* (2006.01)

(52) U.S. Cl.
CPC ............... *A61M 5/46* (2013.01); *A61M 5/3202* (2013.01); *A61M 5/326* (2013.01); *A61M 5/3213* (2013.01); *A61M 5/3257* (2013.01); *A61M 5/3243* (2013.01); *A61M 5/3271* (2013.01); *A61M 5/347* (2013.01); *A61M 2005/3247* (2013.01); *A61M 2005/3254* (2013.01); *A61M 2005/3263* (2013.01); *A61M 2005/3267* (2013.01)

(58) Field of Classification Search
CPC ..... A61M 5/24; A61M 5/3271; A61M 5/326; A61M 2005/3254; A61M 25/0631
USPC ......... 604/201, 187, 192, 194, 197, 198, 244, 604/506, 207, 246
See application file for complete search history.

(56) References Cited

U.S. PATENT DOCUMENTS

| | | |
|---|---|---|
| 5,542,760 A | 8/1996 | Chanoch et al. |
| 5,961,495 A | 10/1999 | Walters et al. |
| 6,096,010 A | 8/2000 | Walters et al. |
| 6,221,053 B1 | 4/2001 | Walters et al. |
| 6,248,095 B1 | 6/2001 | Giambattista et al. |
| 6,277,099 B1 | 8/2001 | Strowe et al. |
| 6,585,698 B1 | 7/2003 | Packman et al. |
| 6,932,794 B2 | 8/2005 | Giambattista et al. |
| 6,936,032 B1 | 8/2005 | Bush, Jr. et al. |
| 7,018,364 B2 | 3/2006 | Giambattista et al. |
| 7,645,264 B2 | 1/2010 | Marsh et al. |
| 7,850,663 B2 | 12/2010 | Sullivan et al. |
| 2010/0286605 A1 | 11/2010 | Klug et al. |
| 2011/0257603 A1* | 10/2011 | Ruan et al. .................... 604/198 |
| 2011/0288491 A1 | 11/2011 | Newman et al. |
| 2012/0172793 A1 | 7/2012 | Cronenberg et al. |

FOREIGN PATENT DOCUMENTS

WO    WO 2006-123251    11/2006

OTHER PUBLICATIONS

European Search Report and Opinion issued for European Patent Application No. EP14180046, dated Oct. 16, 2014.

* cited by examiner

*Primary Examiner* — Nathan R Price
*Assistant Examiner* — Anh Bui
(74) *Attorney, Agent, or Firm* — Dickinson Wright PLLC

(57) ABSTRACT

A shielded pen needle assembly is provided in which the hub extends distally beyond an outer sleeve of the assembly.

16 Claims, 4 Drawing Sheets

FIG. 1
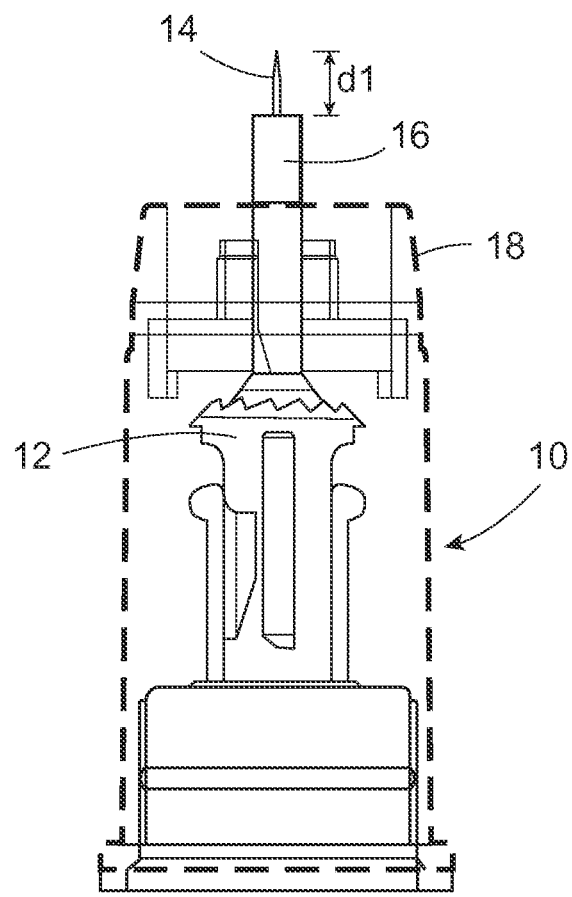
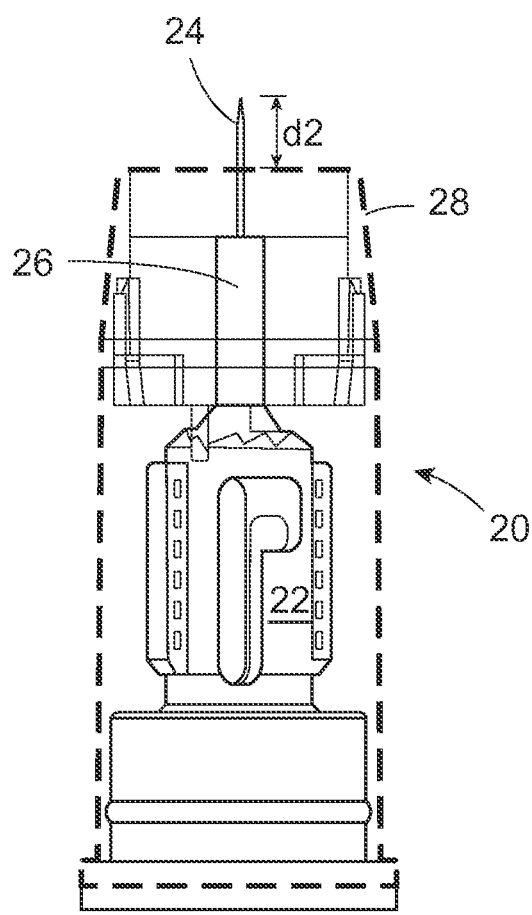
FIG. 2
Prior Art

000# EXTENDED HUB FOR A SAFETY PEN NEEDLE

BACKGROUND OF THE INVENTION

1. Field of the Invention

The invention is in the field of injection devices having an automated shield for covering the needle after an injection, and specifically the invention is directed to a safety pen needle having an extended hub.

2. Description of the Related Art

The prior art teaches various safety shield systems adapted for use with a medication pen. Examples of passive shielding systems include those described in U.S. Patent Application Publication Nos. 2011/0288491 and 2011/0257603, which are incorporated by reference. Typically, the penetration depth of the needle in a shielded medication pen is defined by the distance from the needle tip to the distal end of an outer sleeve, which forms an outer periphery of the device. The inventor has explored a pen needle shield system in which the injection depth of the needle is defined without reference to the position of the outer sleeve.

SUMMARY OF THE INVENTION

Thus, in one aspect, the invention is a pen needle assembly incorporating a passive shield adapted to cover the needle cannula after an injection. The assembly comprises a hub adapted to receive a medication pen body having a medication compartment therein. A needle cannula is affixed to the hub having a distal end extending from the distal end of the hub and a proximal end adapted to access the medication compartment in the pen body. The passive shield is provided on the assembly with a biasing member biasing the passive shield to a distal position covering the needle cannula after injection. An outer sleeve attached to the hub encircles the passive shield and the hub. The hub is extended with respect to the pen body, so that the distal end of the hub is located distally of the distal end of the outer sleeve. Thus, the distance between the distal tip of the needle and the distal end of the hub is the effective penetration depth of the needle.

In a preferred embodiment, a pen needle assembly according to the invention comprises an extended hub adapted to receive a medication pen body having a medication compartment therein. A needle is affixed to the hub having a distal end extending from the distal end of the hub, and a proximal end adapted to access the medication compartment in the pen body, as described above. The distal end of the hub is positioned distally of the outer sleeve. An inner shield on the hub encircles the needle, so that the distal end of the needle protrudes therefrom in an initial position, and a spring biases the inner shield in the distal direction. An outer shield encircles the inner shield and releasably retains the inner shield in the initial position against the bias of the spring. Proximal movement of the outer shield during an injection releases the inner shield to move under bias of the spring to cover the distal end of the needle in an after-use position.

Thus, in the embodiments described above, the effective penetration depth of the needle cannula is from the distal tip of the needle to the distal end of the hub. When the patient or health care professional administers an injection, the injection force is concentrated on the relatively small area of the distal end of the hub rather than being distributed to the ring formed by the outer sleeve. The device facilitates appropriate insertion depth compared to prior art safety shield devices because the concentration of force on the distal end of the hub prevents the spring-biased inner shield from moving past that point on the hub, whereas, distributing force on the outer sleeve, as in the prior art, may permit the inner shield to protrude distally beyond the outer sleeve, potentially limiting the injection depth.

Where the passive safety shield is urged in a distal direction to cover the needle cannula after administering an injection, the passive shield need only move from the distal end of the hub to a position covering the needle. Because less spring force is required to power the passive shield this short distance, less sensible pressure is exerted against the patient's tissue.

Except for the hub extension, the parts of the shield assembly are similar to, and in some embodiments, identical to, prior art shield systems. Consequently, designs are changed over easily, and interoperability of many parts is ensured.

BRIEF DESCRIPTION OF THE DRAWINGS

FIG. 1 depicts a partial pen needle assembly according to the invention with the hub extended distally past the outer sleeve.

FIG. 2 depicts a partial pen needle assembly design according to the prior art, showing the effective length of the needle cannula projecting from the distal end of the outer sleeve.

DETAILED DESCRIPTION OF THE INVENTION

Figure 3:
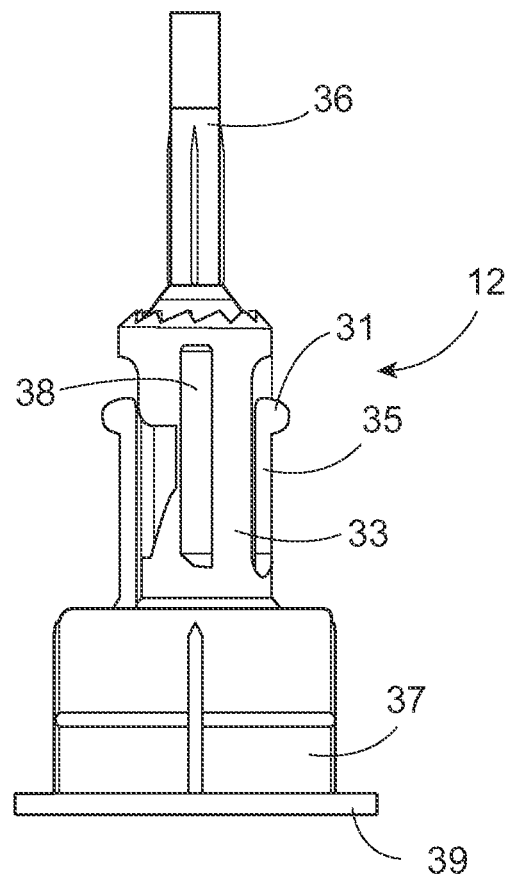
FIG. 3 depicts an extended hub according to one embodiment of the invention.

As used herein, the "distal" direction is in the direction of the injection site, and the "proximal direction" is the opposite direction. The "axial" direction is along the longitudinal axis of the injection device. The needle cannula is generally arranged axially in the device. "Radially" is a direction perpendicular to the axial direction. Thus, "radially inward" generally means closer to the needle. "Integral" means one-piece in the state normally encountered by the user—not intended to be taken apart easily. A "passive" shield is a shield on an injection device which is urged automatically into a position covering the needle cannula after an injection is administered without requiring manipulation by the user or health care professional.

FIG. 1 shows a partial pen needle assembly 10 including the extended hub post 16 on hub 12 positioned distally of the outer sleeve 18 which is shown in outline. The inner and outer sleeves are removed from FIG. 1 to more clearly delineate the position of the needle cannula 14 with respect to the outer sleeve 18. The distance $d_1$ is the effective penetration depth of the needle, measured from the tip of the needle cannula to the distal end of the hub 16. In comparison, a prior art assembly 20 is represented in FIG. 2, where the effective penetration depth of the needle is $d_2$, measured from the distal end of the outer sleeve 28 to the tip of the needle cannula 24. The effective penetration depth is not particularly limited according to the invention, but operable embodiments of the invention include a penetration depth of 8 mm, 6 mm, 5 mm, and 4 mm, all for subcutaneous injection. Shorter effective cannula lengths may be used for intradermal injection devices, and the extended hub will facilitate proper insertion across all intradermal and subcutaneous cannula lengths.

FIG. 3 depicts the hub 12 according to the invention adapted to have the needle cannula fixed in a central bore thereof, and adapted to receive a medication pen body. In preferred embodiments, the hub 12 comprises a body portion 33, a post portion 36 which is narrower than the body portion 33, and a base portion 37 which is wider than the body portion 33. The base portion 37 may be provided with threads or other features on an interior surface thereof adapted to receive the pen body. The distal post 36 is slightly extended compared to a conventional hub post, while the remainder of the hub 12, the body portion 33 and base portion 37, may be sized to ensure interoperability with existing medication pen devices. In this embodiment, the hub body 33 includes protrusions 38 which receive the passive shield to prevent the shield from rotating. The hub body 33 may also include extending flexible arms 35 with protrusions 31 to retain the shield in an initial proximal position.

Figure 4:
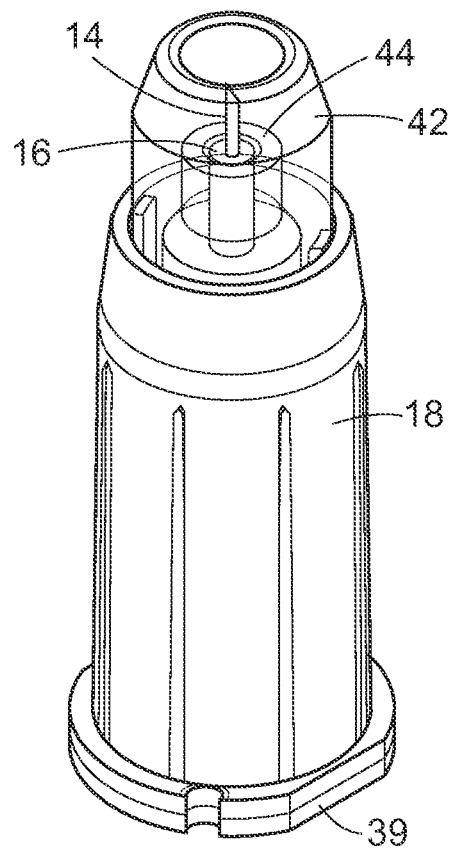
FIG. 4 is a perspective view of the pen needle according to one embodiment of the invention in a state prior to use.

In preferred embodiments, which should not be construed as limiting the invention, the shield assembly includes passive inner shield 44 and outer shield 42 encircling the needle 14 as shown in FIG. 4. In the embodiment shown in FIG. 4, needle 14 is affixed to the hub 12 and extends distally from hub post 16 on the distal end of the hub. The needle 14 includes a proximal end adapted to access the medication compartment in the pen body. The needle is fixed on the hub with adhesive or mechanical lock or other means, so that the effective penetration depth $d_1$ of the needle extends from the distal end of the hub post. The proximal end of needle extends within a cavity formed on the interior of base portion 37 of the hub but preferably does not extend in a proximal direction beyond a plane formed by the bottom flange 39 of the hub. This allows the assembly to be shipped with a peelable flexible cover over the opening on the base 37 of the hub.

Figure 8:
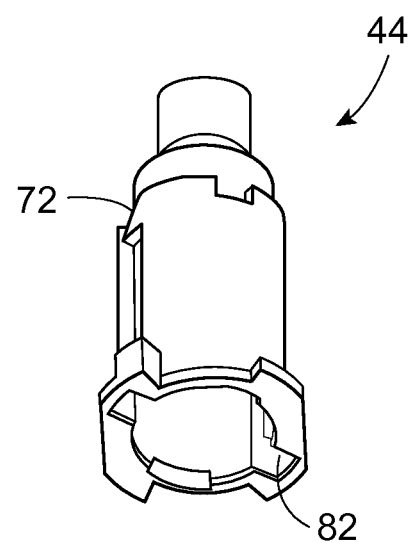
FIG. 8 is perspective view of the inner shield depicted in FIG. 6.

In this embodiment, the inner shield 44 includes lobes 82, shown in FIG. 8, which engage protrusions 38 on the hub and ensure that the inner shield does not rotate during proximal movement of the outer shield 42 into sleeve 18. Likewise, the inner shield 44 does not rotate when moved distally over the needle cannula after an injection under bias of the spring.

Figure 5:
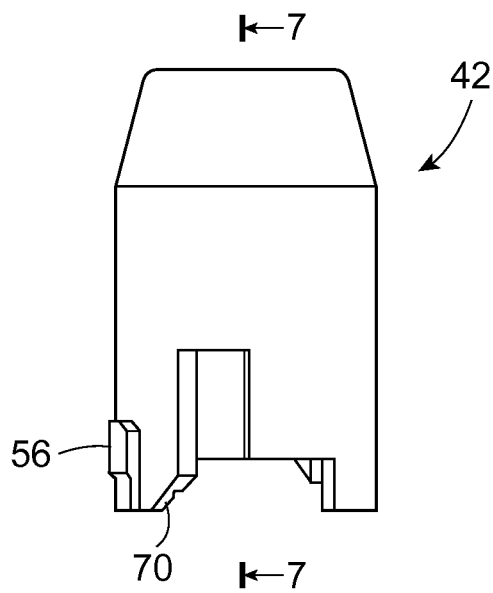
FIG. 5 is an outer shield according to one embodiment of the invention.
Figure 6:
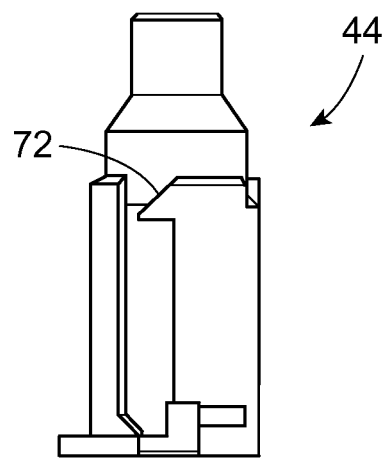
FIG. 6 is an inner shield according to an embodiment of the invention.
Figure 7:
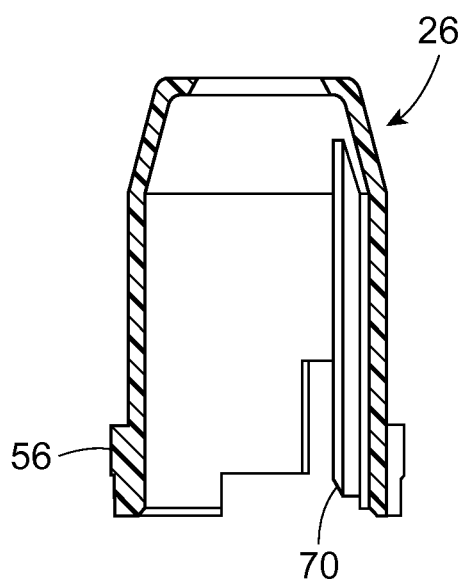
FIG. 7 is a cross sectional view the outer shield depicted in FIG. 5.

Outer shield 42 encircles the inner shield 44 and covers the needle 14 in the initial position prior to use. As shown in FIG. 5, outer shield 42 is provided with detents 56 adapted to engage recesses in an interior surface of the outer sleeve 18 to control the path of the outer shield 42 when it is pressed into the outer sleeve 18 during an injection. Proximal movement of the outer shield 42 during an injection releases the inner shield 44 under bias of the spring to cover the distal end of the needle in an after-use position.

Figure 9:
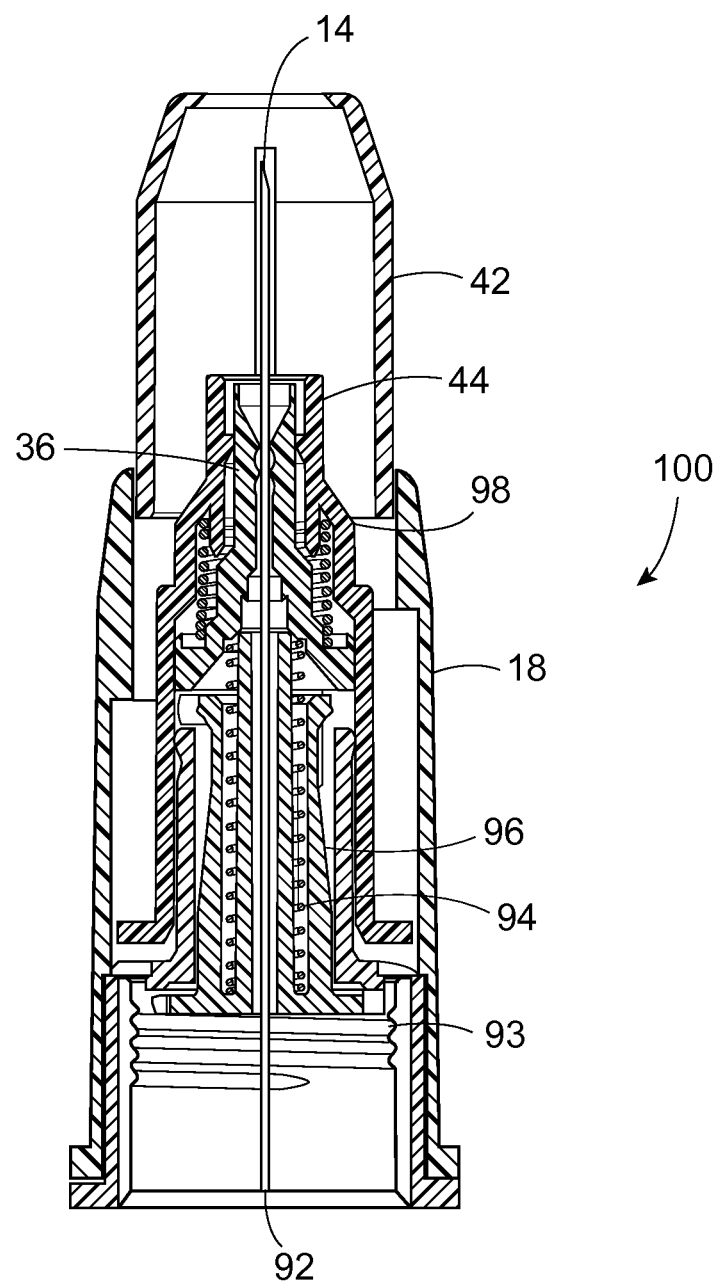
FIG. 9 is a cross sectional view of a pen needle assembly including a non-patient end shield according to another embodiment of the invention.

The embodiment of FIG. 9 includes inner and outer shields interacting with the hub and outer sleeve as described above, and further includes a passive non-patient end shield 96 which automatically covers the non-patient end of the needle cannula when the pen needle is removed from the pen body. The operation of the full dual-shield embodiment is substantially as described in the aforesaid U.S. Patent Application Publication 2011/0257603, incorporated by reference for this purpose.

During an injection, outer shield 42 is pressed against the injection site and the user presses the medication pen so that the needle cannula enters the patient's tissue. The distal end of the inner shield 44 is preferably at or proximal of the distal end of the hub post 16, although there may be some slight proximal movement of the inner shield 44 while the inner shield is pressed against the patient's tissue before the needle reaches full penetration depth. In the extended hub design, pen insertion force against the skin is focused onto the top of the hub post 16, which is a relatively small surface area. This allows for deeper cannula penetration compared to prior art designs, where the outer sleeve contacts the area around the injection site and distributes the insertion force in a ring around the injection site formed by the outer sleeve.

Detents 56 on the outer shield 42 are guided in grooves located on an interior surface of the outer sleeve 18 so that initial proximal movement of the outer shield 42 is in the axial direction only, without rotation. After the detents 56 clear the grooves on the outer sleeve 18, the outer shield is able to rotate as respective tapered surfaces 70, 72 on the inner shield 42 and outer shield 44 slide against one another. As the tapered surface 70 comes out of engagement with surface 72, the inner shield is able to move distally to cover the distal end of the needle cannula 14 under bias of the spring 98.

The force exerted against the skin by spring-biased inner shield 44 as it moves to cover the needle cannula is potentially lower than in prior art pen needle assemblies because the inner shield may be positioned distally of the outer sleeve 18, which is therefore closer to the distal end of the needle cannula. Thus passive shield 44 travels a shorter distance. Correspondingly less force is required to maintain the shield at or below the hub post during injection. These factors likely allow for insertion closer to the optimal depth to be achieved.

In the after-use state, the inner shield 44 preferably protrudes through an opening on the distal end of the outer shield 42. The inner shield 44 is formed with a narrow portion which fits through the opening, and a wider shoulder portion which contacts the outer shield in the after-use state. Preferably means for locking out the inner shield 44 after use are provided to ensure that the needle cannula cannot be re-exposed. For example, protrusions on the inner shield mating with recesses on the outer sleeve 18 may be provided. Alternatively, the inner shield 44 could be locked out against the hub. Other configurations would be apparent to those of ordinary skill in the art.

The pen needle may be shipped with a protective outer cap on the distal side of the shield assembly which mates with the outer sleeve in an interference fit. A flexible peelable cover may be provided over an opening on the proximal side of the assembly, sealing the protective outer cap, the outer sleeve and the hub within and maintaining product sterility. To install the pen needle assembly on a medication pen, the user peels the flexible protective cover from the opening, exposing the features 93 on the hub adapted to receive the pen. When the pen needle assembly is threaded on to the pen (or connected by latches or other means securing the hub to the pen body), the protective outer cover can be pulled off.

The proximal end shield 96 likewise may be releasably retained in an initial position, and locked out under force of spring 94 after use by removing the pen needle assembly from the pen body, as disclosed in the aforesaid Patent Application Publication No. 2011/0257603. Alternatively some other means of passively shielding the proximal end 92 of the needle cannula may be employed without departing from the scope of the invention.

The above description of the preferred embodiments is not to be deemed limiting of the invention, which is defined by the appended claims. Features disclosed in connection with one embodiment may be combined in another embodiment without departing from the scope of the invention.

The invention claimed is:

1. A pen needle assembly, comprising:
   a hub adapted to receive a medication pen body having a medication compartment therein;
   a needle cannula affixed to the hub having a distal end extending from the distal end of the hub and a proximal end adapted to access the medication compartment in the pen body;
   a first passive shield with a distal end at or proximal of the distal end of the hub in an initial position arranged on the hub and encircling the needle cannula;
   a biasing member biasing the first passive shield to a distal position covering the needle cannula after injection;
   an outer sleeve attached to the hub having a distal end encircling the first passive shield and the hub;
   an outer shield radially outward of the first passive shield and radially inward of said outer sleeve, said outer shield covering the needle cannula in an initial state prior to use;
   the outer shield having a retaining feature retaining the first passive shield in the initial position and not engaging the first passive shield radially, wherein rotating movement of the outer shield frees the first passive shield from the retaining feature so that the first passive shield moves distally under urging of the biasing member to cover the needle cannula in an after-use position; and
   wherein the distal end of the hub extends beyond the distal end of the outer sleeve, and the distance between the distal tip of the needle and the distal end of the hub is the effective penetration depth of the needle.

2. The pen needle assembly according to claim 1, further comprising a passive proximal end shield and a second biasing member biasing the passive proximal end shield to cover the proximal end of the needle cannula after an injection.

3. The pen needle assembly according to claim 1, wherein said distance between the distal tip of the needle and the distal end of the hub defining the effective penetration depth of the needle is in a range of 4 mm to 8 mm.

4. The pen needle assembly according to claim 1, wherein said distance between the distal tip of the needle and distal end of the hub defining the effective penetration depth of the needle is an intradermal injection depth.

5. The pen needle assembly according to claim 1, wherein the hub comprises a body portion and a post portion, wherein the post portion is narrower than the body portion and located distally of the body portion; wherein the first passive shield is received over the hub so that lobes on the first passive shield engage protrusions on the hub to prevent rotation of the first passive shield; further comprising
   an outer shield radially outward of the first passive shield having a retaining feature retaining the first passive shield in an initial position, wherein proximal movement of the outer shield frees the first passive shield from the retaining feature so that the first passive shield moves distally under urging of the biasing member to cover the needle cannula in an after-use position; and
   a passive proximal end shield biased by a second biasing member to cover the proximal end of the needle cannula after an injection.

6. A pen needle assembly, comprising:
   a hub adapted to receive a medication pen body having a medication compartment therein;
   a needle affixed to the hub having a distal end extending from the distal end of the hub and a proximal end adapted to access the medication compartment in the pen body;
   an inner shield at or proximal of the distal end of the hub in an initial position encircling the needle, so that the distal end of the needle protrudes therefrom in an initial position;
   a spring biasing the inner shield in the distal direction;
   an outer shield encircling the inner shield and not engaging the inner shield radially and releasably retaining the inner shield in said initial position against the bias of the spring wherein rotating movement of the outer shield frees the inner shield from the retaining feature so that the inner shield moves distally under urging of the biasing member to cover the needle cannula in an after-use position; and
   a sleeve encircling the outer shield;
   wherein the distal end of the hub extends beyond the distal end of the sleeve and the distance between the distal tip of the needle and the distal end of the hub is the effective penetration depth of the needle.

7. The pen needle according to claim 6, wherein the effective penetration depth of the needle is 4 mm to 8 mm.

8. The pen needle according to claim 6, wherein the effective penetration depth is an intradermal injection depth.

9. The pen needle according to claim 6, wherein the hub has a body portion and a post portion located distally of the body portion, wherein the post portion extends distally beyond the sleeve, and wherein the body portion does not extend distally beyond the sleeve.

10. The pen needle according to claim 6, further including a second spring and a proximal end passive shield, wherein the second spring biases the proximal end shield over the proximal end of the needle cannula after an injection.

11. A method of administering an injection to a patient and passively shielding a needle cannula of a medication pen, comprising:
    installing a pen needle assembly comprising a needle-bearing hub on a medication pen body having a medication compartment therein so that a needle cannula affixed to the hub extends distally from the distal end of the hub and a proximal end of the needle accesses a medication compartment in the pen body;
    providing on said pen needle assembly a first passive shield having a distal end, a first biasing member urging the first passive shield distally, and an outer sleeve having a distal end encircling the first passive shield, said distal end of the outer sleeve located proximally of the distal end of the hub, and the distal end of the first passive shield at or proximal of the distal end of the hub in an initial position;
    providing an outer shield on the pen needle assembly radially outward of the first passive shield and radially inward of the outer sleeve, said outer shield covering the needle cannula in an initial state prior to use;
    retaining the first passive shield in an initial position with the needle cannula protruding from a distal end thereof;
    applying pressure to the medication pen so that the needle cannula enters the patient's tissue to an effective penetration depth defined by the distance between the distal tip of the needle and the distal end of the hub;
    releasably retaining the first passive shield in the initial position by contact of the outer shield and the first passive shield and not engaging the first passive shield radially with the outer shield; and
    moving the outer shield proximally during an injection and rotating to release the first passive shield;
    releasing the first passive shield to a distal position covering the needle cannula after injecting medication and removing the needle from the patient's tissue.

12. The method according to claim 11, further comprising
providing on the pen needle assembly a passive proximal end shield urged in the proximal direction by a second biasing member; and
removing the pen needle assembly from the pen body after an injection causing the proximal end shield to cover the proximal end of the needle cannula.

13. The method according to claim 11, comprising positioning the first passive shield distally of the outer sleeve in said initial position, reducing the force required to maintain the first passive shield at or proximally of the distal end of the hub.

14. The method according to claim 11, wherein the injection is a subcutaneous injection and the penetration depth is in a range of 4 mm to 8 mm.

15. The method according to claim 11, wherein the injection is an intradermal injection.

16. The method according to claim 12, comprising locking out the first passive shield in a position covering the distal end of the needle.

\* \* \* \* \*